United States Patent [19]

Astbury et al.

[11] Patent Number: 5,382,741
[45] Date of Patent: Jan. 17, 1995

[54] PROCESS FOR THE PRODUCTION OF MONO-OLEFINS

[75] Inventors: Christopher J. Astbury, London; David C. Griffiths, Surrey; Mark J. Howard, North Humberisde; Ian A. B. Reid, London, all of England

[73] Assignee: The British Petroleum Company p.l.c., London, England

[21] Appl. No.: 912,184

[22] Filed: Jul. 13, 1992

[30] Foreign Application Priority Data

Aug. 9, 1991 [GB] United Kingdom ............... 9117216

[51] Int. Cl.$^6$ .............................................. C07C 5/333
[52] U.S. Cl. .................................. 585/652; 585/654; 585/658; 585/660
[58] Field of Search ................ 585/658, 659, 660, 652

[56] References Cited

U.S. PATENT DOCUMENTS

| | | | |
|---|---|---|---|
| 2,817,690 | 12/1957 | Lobo | 260/679 |
| 2,962,362 | 11/1960 | Moorman | 585/659 |
| 3,541,179 | 11/1970 | Okagami et al. | 260/683.3 |
| 3,670,044 | 6/1972 | Drehman et al. | 260/683.3 |
| 3,692,862 | 9/1972 | Staud | 585/652 |
| 3,793,225 | 2/1974 | Bertus et al. | 252/437 |
| 4,663,493 | 5/1987 | Vora et al. | 585/655 |
| 4,940,826 | 7/1990 | Font Freide et al. | 585/600 |

FOREIGN PATENT DOCUMENTS

| | | |
|---|---|---|
| 0178853 | 4/1986 | European Pat. Off. . |
| 0196758 | 10/1986 | European Pat. Off. . |
| 0332289 | 9/1989 | European Pat. Off. . |
| 0323115 | 10/1989 | European Pat. Off. . |
| 1113102 | 3/1956 | France . |
| 1250763 | 12/1960 | France . |
| 1156193 | 10/1963 | Germany . |

OTHER PUBLICATIONS

F. M. Ashmaury "Catalytic Oxidative Dehydrogenation . . . " Journal of Catalysts, vol. 46, 1977 pp. 424–425.

*Primary Examiner*—Asok Pal
*Assistant Examiner*—P. Achutamurthy
*Attorney, Agent, or Firm*—Nixon & Vanderhye

[57] ABSTRACT

A process for the production of mono-olefins from a paraffin-containing hydrocarbon feed having at least two carbon atoms which comprises a first step of partially combusting a mixture of the hydrocarbon feed and a molecular oxygen-containing gas in contact with a catalyst capable of supporting combustion beyond the normal fuel rich limit of flammability, the first step being carried out under a total pressure of greater than 5 bar absolute and at a temperature of greater than 650° C.; and a second step of cooling the mono-olefinic products to 600° C. or less within less than 50 milliseconds of formation.

11 Claims, No Drawings

PROCESS FOR THE PRODUCTION OF MONO-OLEFINS

The present invention relates to a process for the production of mono-olefins from a hydrocarbon feed.

A known commercial route to the production of olefins is via steam cracking of paraffinic hydrocarbons. Steam cracking involves the pyrolysis of the hydrocarbons and in general, the conditions which favour maximum conversion and maximum olefin production are (1) a highly saturated feed, (2) a high furnace outlet temperature and (3) low hydrocarbon partial pressure. In particular, the process must be carried out under low hydrocarbon partial pressure, typically less than one atmosphere.

Possibly, the simplest reaction in the aforementioned process is the cracking of ethane:

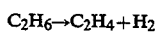

Considering this reaction, it is of course apparent that the number of moles of product will exceed the number of moles of reactant. Thus, if the partial pressure of the paraffinic hydrocarbon is increased, the reaction is likely to favour hydrogenation over the cracking reaction. Conventional understanding thus indicates that if elevated pressure is used in this process, conversion and selectivity to olefins will be low.

Indeed, this teaching is disclosed in various published papers and textbooks including "Mono-olefins—Chemistry and Technology" by F Asinger, Pergammon Press, 1968, pp 62–63, 91, 121 and 125; Chem Systems Report No 83-6, September 1984, and Chem Systems Report No 89S8, March 1991. The aforementioned disclosures indicate that low hydrocarbon partial pressure is essential to suppress secondary reactions of the olefinic products thus maximising the yield of olefins.

Olefins can also be prepared by cracking a paraffinic feed wherein the heat required for pyrolysis is provided by the partial combustion of the feedstock and not by the conventional tubular fired heaters. This process for the production of olefins is described in our published European patent application No 0332289. The process can be described as "autothermal cracking" of paraffins and will be referred to as such hereafter.

The autothermal cracking process provides the advantage over conventional steam cracking in that the reactor is simpler, there is less soot formation and the once through yield of olefins can be improved. As found in steam cracking, maximum yield of olefins is obtained if the process is carried out under low pressure, typically 1 atmosphere or less. The use of elevated pressure in the autothermal cracking process results in products which are richer in methane and carbon monoxide.

Surprisingly, we have now found that high olefin yields can be obtained in the autothermal cracking of hydrocarbons at elevated pressure provided the products are rapidly cooled.

Accordingly, the present invention is a process for the production of mono-olefins from a paraffin-containing hydrocarbon feed having at least two carbon atoms, the process comprising (A) a first step of partially combusting a mixture of the hydrocarbon feed and a molecular oxygen-containing gas in contact with a catalyst capable of supporting combustion beyond the normal fuel rich limit of flammability, said first step carried out under a total pressure of greater than 5 bar absolute and at a temperature of greater than 650° C., and (B) a second step of cooling the mono-olefinic products to 600° C. or less within less than 50 milliseconds of formation.

The conversion of the hydrocarbons to mono-olefins can be successfully achieved with high yields by carrying out the process at elevated pressure which is, of course, contrary to conventional wisdom. By employing a rapid cooling step, the olefinic products are preserved without a significant loss to the yield.

The cooling step slows down the rates of reactions in the gaseous product stream thus preventing further reactions taking place. The time between formation of the olefinic products and cooling, hereafter referred to as the residence time, is very short, typically less than 50 milliseconds.

A short residence time of less than 50 ms is essential for high pressure autothermal cracking to preserve the olefinic products. In sharp contrast, the magnitude of the residence time at atmospheric pressure is of less significance, with operation at short residence time optional. Indeed, a longer residence time in excess of 100 ms is preferable at low pressure to maximise conversion and ethylene yield.

Additionally, the use of elevated pressure provides the advantage that smaller sized equipment is required with the elimination of compression stages in the downstream processing train. These benefits lead to a more compact, more efficient process and a reduction in overall capital costs.

The hydrocarbon feed may be suitably ethane, propane, butane or paraffin-containing hydrocarbons such as naphtha, gas oil, vacuum gas oil or mixtures thereof. Additional feed components may be included, if so desired. Suitably, methane, nitrogen, carbon monoxide, carbon dioxide, steam or hydrogen may be co-fed into the reactant stream. It is preferred, although not essential, to co-feed hydrogen into the reactant stream. By doing so, the yields of, and selectivities to, the desired products may be improved. The formation of carbon monoxide and carbon dioxide may also be reduced.

The hydrocarbon feed is mixed with a molecular oxygen-containing gas. Suitably, the gas is oxygen, optionally diluted with an inert gas such as nitrogen. It is preferred to pre-mix the oxygen containing gas and the paraffinic feed prior to contact with the catalyst.

The composition of the hydrocarbon/molecular oxygen-containing gas mixture is suitably from 5 to 13.5 times the stoichiometric ratio of hydrocarbon to oxygen containing gas for complete combustion to carbon dioxide and water. The preferred composition is from 5 to 9 times the stoichiometric ratio of hydrocarbon to oxygen containing gas.

A catalyst capable of supporting combustion is employed in the present process. The principal role of the catalyst is to stabilise partial combustion of the gaseous mixture which may not otherwise be flammable.

Suitably, the catalyst is a supported platinum group metal. Preferably, the metal is either platinum or palladium or a mixture thereof. Although a wide range of support materials are available, it is preferred to use alumina as the support. The support material may be in the form of spheres, other granular shapes or ceramic foams. Preferably, the form is a monolith which is a continuous multichannel ceramic structure, frequently of a honeycomb appearance.

A preferred support for the catalyst is a gamma alumina coated lithium aluminium silicate foam. The support is loaded with a mixture of platinum and palladium by conventional methods well known to those skilled in the art. The resulting compound is then heat treated to 1200° C. before use in the process of the present invention.

The catalyst may be used as a fixed bed or as a solids recirculating bed e.g. a fluid or spouted bed. It is preferred to use the catalyst in a fixed bed mainly because problems with attrition, which are mainly encountered in moving bed operations, may be avoided.

The process is carried out at a temperature greater than 650° C. e.g. suitably greater than 750°, preferably greater than 800° C. The upper temperature limit may suitably be up to 1200° C., preferably up to 1100° C.

It is preferred, although not essential, to pre-heat the feed gas and the oxygen containing gas to suitably 200°–500° C., preferably 200°–300° C. The gases may be separately pre-heated or pre-heated following mixing.

Preferably, the gaseous feed mixture is introduced into the reaction chamber under a gas hourly space velocity of greater than 80,000 hr$^{-1}$ in order to minimise the formation of carbon monoxide and carbon dioxide. Preferably, the gas hourly space velocity exceeds 200,000 hr$^{-1}$ especially greater than 1,000,000 hr$^{-1}$. For the purposes of the present invention, gas hourly space velocity is defined as:

$$GHSV = \frac{\text{volume of total feed at } NTP}{\text{Time} \times \text{volume of catalyst bed}}$$

It is essential to the present process, that the reaction takes place under elevated pressure. A total pressure of greater than 5 bar absolute is employed.

The cooling step will of course prevent degradation of, and/or further reactions between, the olefinic products and may suitably be carried out using rapid heat exchangers of the type familiar in steam cracking technology. Also possible, either additionally or instead of these indirect heat exchangers, a direct quench may suitably be employed. Suitable quenching fluids include water.

A hydrocarbon quenching fluid may also be used to reduce the product temperature. At the aforementioned temperature and pressure, some of the hydrocarbon fluid may be cracked to provide additional olefinic products in the effluent stream. The use of elevated pressure advantageously accelerates the rate of pyrolysis of such quenching fluids and leads to an increase in olefin yield. Such hydrocarbon fluids are generally referred to as reactive quenching fluids. Suitably, the reactive quench may be a naphtha compound. Optionally, a second quenching fluid, such as water, may be employed.

It will of course be understood that the amount of quenching fluid which may be usefully employed will depend upon the temperature of the effluent stream.

The products of the present invention include ethene, propene, butene and pentene, higher olefins and alkanes. In addition to these products, small amounts of methane, acetylenes, aromatics, water, hydrogen, carbon dioxide and carbon monoxide may be produced. It is of course understood that the composition of the product stream will depend upon the feedstock.

The process of the invention will now be further illustrated by reference to the following Examples.

EXAMPLE 1

Preparation of Ceramic Foam Catalysts

The lithium aluminium silicate foam support was obtained precoated with gamma alumina from Morgan Matroc plc with a porosity of 30 ppi. The foam was washed with a platinum/palladium solution of tetraammine metal chloride salts, drawn through the support by vacuum, dried, and finally calcined to 1200° C. for 12 hours. The impregnation of the foam was controlled by monitoring the volume of solution absorbed by the foam to give a loading of 0.25 wt % in the final catalyst.

EXAMPLE 2

The Pt/Pd loaded ceramic foam catalyst (approximately 15 mm diameter×30 mm length) was placed at the bottom of a quartz reactor consisting of a feed section 70 mm in length, 5 mm in diameter and reactor section 15 mm in diameter and 80 mm in length. The reactor was connected to a gas feed system, insulated and fitted into a pressure jacket. A water quench probe was located approximately 80 mm down stream of the reactor.

Propane, hydrogen, nitrogen and oxygen were preheated to 200° C. to effect autothermal operation, where the exothermic heat of combustion raised the heat required to pyrolyse propane. The reaction was carried out at 800°–1000° C. and under elevated pressure, typically 10 or 11 bar absolute. The products were cooled within 20 milliseconds of formation. Details of the composition of the feed, the flow rates and the results obtained are given in Table 1.

EXAMPLE 3

In accordance with the current invention, a sulphur contaminated naphtha hydrocarbon feed was processed in the reactor as described in Example 2. Benzene content in the hydrocarbon feed was 2.7 wt % with a toluene content of 1 wt %. To obtain catalytic light up, ethane was initially fed to the reactor (0.9 liters/minute) with hydrogen (0.64 liters/minute) and nitrogen (0.18 liters/minute), with the feed preheated to 200° C. Nitrogen was added as an internal standard for subsequent product analysis by gas chromatography and is not required for operation of the process of the present invention. A pressure of 5 bars was established prior to admittance of oxygen (0.6 liters/minute). The temperature was seen to rise to the nominal operating temperature 900° C. The ethane feed was then gradually substituted by the sulphur contaminated hydrocarbon feed. The reaction was carried out at 800°–1000° C., and under a pressure of 5.1 bar absolute. The products were quenched within 20 milliseconds of formation. Details of the feed composition, flow rates and the results obtained are given in Table 2.

Comparative Example 1

Example 1 was repeated but with a longer residence time of 220 milliseconds. Details of the composition of the feed, the flow rates and the results obtained are give in Table 3. It can be seen that the yield of, and selectivity to ethylene are reduced when the products are not cooled within 50 milliseconds of formation.

Comparative Example 2

Into a 30 mm diameter quartz reactor as used in Example 1, was placed a catalyst in the form of previously calcined Pt/Pd gamma alumina spheres (2 mm diameter), supported on a silica sintered disk. The preparation of this catalyst is detailed in EP-A-0332289. Propane, hydrogen, oxygen and nitrogen were passed over the catalyst under atmospheric pressure in the molar proportions, and under the conditions, as shown in Table 4. It is evident from these results that high conversion and high selectivity to ethylene is possible under atmospheric pressure provided the residence time is relatively high.

TABLE 1

| GHSV ($\times 10^6$ hr$^{-1}$) | Total Flow (nl/min) | $C_3H_8/O_2$ | $H_2/O_2$ | Total Pressure (bara) | Residence Time (ms) | Conversion (% mol) | Selectivity (% C mol) | | | | | |
|---|---|---|---|---|---|---|---|---|---|---|---|---|
| | | | | | | | $C_2H_4$ | $C_2H_2$ | $CH_4$ | CO | $CO_2$ | Coke |
| 3.0 | 266 | 1.77 | 0.94 | 10.5 | 20 | 97.9 | 36.5 | 0.4 | 26.1 | 19.3 | 2.1 | 0 |
| 3.1 | 278 | 1.96 | 0.94 | 10.2 | 20 | 95.4 | 36.6 | 0.1 | 24.2 | 17.4 | 1.7 | 0 |
| 3.2 | 280 | 1.90 | 1.06 | 11.0 | 20 | 95.6 | 37.0 | 0.5 | 22.0 | 13.2 | 2.1 | 0 |

TABLE 2

| GHSV ($\times 10^6$ hr$^{-1}$) | Total Flow (nl/min) | $H_2/O_2$ | Naphtha/$O_2$ | Yield (wt % C) | | | | | | | | | | | | |
|---|---|---|---|---|---|---|---|---|---|---|---|---|---|---|---|---|
| | | | | $CH_4$ | CO | $CO_2$ | $C_2H_4$ | $C_2H_2$ | $C_2H_6$ | $C_3H_6$ | $C_3H_8$ | $C_4$ | $C_5$ | $C_6H_6$ | $C_6H_7$ | >$C_6$ Liquid |
| 0.99 | 2.09 | 1.12 | 0.64 | 12.77 | 18.43 | 1.93 | 26.97 | 1.06 | 3.34 | 9.22 | 0.53 | 4.72 | 3.51 | 6.31 | 2.78 | 8.45 |
| 0.99 | 2.09 | 1.12 | 0.64 | 13.12 | 19.71 | 1.50 | 25.70 | 1.08 | 3.18 | 7.27 | 0.43 | 2.90 | 3.87 | 5.33 | 3.49 | 12.49 |
| 0.99 | 2.09 | 1.12 | 0.64 | 13.21 | 19.30 | 1.47 | 25.71 | 1.08 | 3.03 | 7.57 | 0.43 | 3.39 | 5.07 | 7.93 | 0.85 | 10.95 |
| 0.99 | 2.09 | 1.12 | 0.64 | 12.08 | 18.52 | 1.28 | 25.37 | 0.80 | 3.34 | 8.84 | 0.49 | 4.16 | 2.26 | 6.78 | 4.30 | 11.78 |

TABLE 3

| GHSV ($\times 10^6$ hr$^{-1}$) | Total Flow (nl/min) | $C_3H_8/O_2$ | $H_2/O_2$ | Total Pressure (bara) | Residence Time (ms) | Conversion (% mol) | Selectivity (% C mol) | | | | | |
|---|---|---|---|---|---|---|---|---|---|---|---|---|
| | | | | | | | $C_2H_4$ | $C_2H_2$ | $CH_4$ | CO | $CO_2$ | Coke |
| 3.0 | 268 | 1.72 | 0.91 | 10.5 | 220 | 99.6 | 11.1 | 0.1 | 38.9 | 19.0 | 7.2 | 16.0 |
| 3.1 | 278 | 1.96 | 0.94 | 11.8 | 220 | 99.2 | 8.8 | 0.1 | 36.9 | 24.8 | 3.7 | 17.0 |

TABLE 4

| GHSV ($\times 10^6$ hr$^{-1}$) | Total Flow (nl/min) | $C_3H_8/O_2$ | $H_2/O_2$ | Total Pressure (bara) | Residence Time (ms) | Conversion (% mol) | Selectivity (% C mol) | | | | |
|---|---|---|---|---|---|---|---|---|---|---|---|
| | | | | | | | $C_2H_4$ | $C_2H_2$ | $CH_4$ | CO | $CO_2$ |
| 0.3 | 26 | 1.99 | 1.22 | 1 | 30 | 75.8 | 39.9 | 0.7 | 16.1 | 9.7 | 2.3 |
| 0.3 | 26 | 1.98 | 1.22 | 1 | 60 | 86.9 | 43.2 | 1.0 | 18.4 | 9.9 | 2.0 |
| 0.3 | 26 | 2.01 | 1.20 | 1 | 90 | 91.0 | 43.8 | 1.4 | 19.1 | 10.2 | 1.8 |
| 0.3 | 26 | 1.94 | 1.20 | 1 | 120 | 92.4 | 44.9 | 1.3 | 19.7 | 10.6 | 1.8 |

We claim:

1. A process for the production of mono-olefins from a paraffin-containing hydrocarbon feed having at least two carbon atoms, the process comprising:
   (a) a first step of partially combusting a mixture of the hydrocarbon feed and a molecular oxygen-containing gas in contact with a combustion catalyst, said first step carried out under a total pressure of greater than 5 bar absolute, and at a temperature of greater than 650° C., and
   (b) a second step of cooling the mono-olefinic products to 600° C. or less within less than 50 milliseconds of formation.

2. A process according to claim 1 in which the hydrocarbon feed is ethane, propane, butane, naphtha, gas oil, vacuum gas oil or mixtures thereof.

3. A process according to claim 1 in which the catalyst is a supported platinum group metal.

4. A process according to claim 1 in which the platinum group metal is platinum or palladium or a mixture thereof.

5. A process according to claim 4 in which the support is alumina.

6. A process according to claims 1 in which the support is a monolith.

7. A process according to claim 1 in which the ratio of the hydrocarbon feed to the molecular oxygen is from 5 to 13.5 times the stoichiometric ratio of hydrocarbon to oxygen for complete combustion to carbon dioxide and water.

8. A process according to claim 1 in which the gaseous feed is introduced at a gas hourly space velocity of at least 80,000 hr$^{-1}$.

9. A process according to claim 1 in which the olefinic product is cooled using rapid heat exchangers or a direct quenching fluid.

10. A process according to claim 9 in which the direct quenching fluid is selected from water or a hydrocarbon compound.

11. A process according to claim 10 in which the hydrocarbon compound is a naphtha compound.

* * * * *